(12) United States Patent
Srivastava et al.

(10) Patent No.: US 7,776,816 B2
(45) Date of Patent: Aug. 17, 2010

(54) PRESERVING HYPOXIC TISSUE

(75) Inventors: Deepak Srivastava, Orinda, CA (US); Ankur Saxena, San Francisco, CA (US)

(73) Assignee: Board of Regents, The University of Texas System, Austin, TX (US)

(*) Notice: Subject to any disclaimer, the term of this patent is extended or adjusted under 35 U.S.C. 154(b) by 765 days.

(21) Appl. No.: 11/336,237

(22) Filed: Jan. 20, 2006

(65) Prior Publication Data

US 2007/0172811 A1   Jul. 26, 2007

(51) Int. Cl.
*A61K 38/00* (2006.01)
*C07K 14/00* (2006.01)
(52) U.S. Cl. ............................. 514/2; 530/351
(58) Field of Classification Search .................. None
See application file for complete search history.

(56) References Cited

OTHER PUBLICATIONS

Yamaguchi et al. Circul 107: 1322-1328, 2003.*
Damas et al. Circul 106: 36-42, 2002.*
Tang et al. 77$^{th}$ Sc Meet of Amer Heart Assoc, Abstract, Circul 110: 169, 2004.*
Koch et al., Basic Res Cardiol 100: 1-9, 2005.*
Tse et al J Pharm Sci 73: 1599-1602, 1984.*

* cited by examiner

*Primary Examiner*—Gary B. Nickol
*Assistant Examiner*—Aditi Dutt
(74) *Attorney, Agent, or Firm*—Richard Aron Osman

(57) ABSTRACT

Hypoxic tissue is preserved by prophylactically administering Stromal Derived Factor 1 Alpha (SDF-1α) before hypoxia induces cell death in the tissue.

21 Claims, No Drawings

PRESERVING HYPOXIC TISSUE

BACKGROUND OF THE INVENTION

The field of the invention is the preservation of hypoxic tissue.

Heart disease is the number one killer of adults in the industrialized world. The majority of acquired heart disease is due to coronary artery disease, in which blood flow to an area of the heart is reduced or eliminated, resulting in death of myocardium and replacement with nonfunctional scar tissue (1, 2). Fatal outcomes are common for individuals suffering acute occlusion of a coronary artery, typically within the first 24 hours.

Hypoxic cardiac tissue post-infarction can be broadly divided into three distinct zones. The direct area of ischemia that has total loss of blood supply sustains largely irreversible cell death and scar tissue-formation. The myocardium immediately surrounding the infarct zone is less severely affected but remains hypoxic. In some cases, cellular changes occur in this area that decrease energy utilization and promote cell survival. This "hibernating myocardium" may eventually recover if neo-angiogenesis or redirection of blood flow restores supply of oxygen and energy substrates (3, 4). Finally, the remaining myocardium typically remains well oxygenated and initially free of damage. The expansion of cell death is a key feature of myocardial infarction as partially ischemic regions of the heart ultimately succumb to hypoxia and are also replaced by scar tissue.

Efficient methods to limit initial loss of myocardium and subsequent expansion of the infarct in the acute period could be of significant value. In fact, overexpression of the survival kinase Akt (protein kinase B) in mesenchymal stem cells injected into mouse hearts postinfarction resulted in a decrease in infarct size (5), possibly as a result of secreted factors from the cells introduced into the heart. Subsequently, work from our laboratory demonstrated that the 43-amino acid protein thymosin β4 activates Akt via integrin linked kinase (ILK) and dramatically protects bordering myocardium from cell death in the first 24 hours after coronary occlusion (6). Given the efficacy of this small protein in our experimental model and the possibility of bypassing hurdles associated with stem cell administration, we investigated the potential for other proteins that activate Akt and have angiogenic properties similar to thymosin β4 to provide beneficial effects post-infarction.

The secreted chemokine stromal cell-derived factor-1α (SDF-1α) and its G-protein-coupled receptor CXCR4 have been implicated in cardiogenesis. Signaling downstream of CXCR4 can trigger a chemotactic response resulting in migration towards an increasing SDF-1α gradient (7-10). In addition, in some cell types, CXCR4 signaling can result in activation of Akt and stimulation of cell proliferation, survival, and angiogenesis (11-17). SDF-1α is upregulated post-infarction (18), and when administered by gene therapy after myocardial infarction reportedly increases homing of bone marrow-derived cells to the area of infarct (19, 20). Itescu (US Pat Pub No. 2005/0233992) discloses administering an inhibitor of SDF-1 to treat myocardial ischemia (MI), and reports that injection of SDF-1 48 hours after triggering MI improved cardiac function through a direct mechanism which involves induction of cardiomyocytes cycling and regeneration and an indirect mechanism operating through enhanced chemotaxis of mobilized bone marrow-derived endothelial progenitors and cardiac neovascularization. Damas et al. reported decreased plasma levels of SDF-1α in patients with coronary artery disease presenting with ischemic chest pain, and suggested that SDF-1α may have a plaque-stabilizing effect and that therapeutic intervention that enhances SDF-1α activity could potentially be beneficial in acute coronary syndromes (Damas, 2002). It has also been reported that SDF-1 administered to an animal model of ischemic hind limb enhanced recruitment and incorporation of transplanted endothelial precursor cells to the ischemic tissue (Yamaguchi, 2003).

We have found that SDF-1α administered to tissue subject to hypoxia prior to hypoxia-induced cell death in the tissue, alters the metabolism of ischemic cells so that they can better withstand hypoxia and evade hypoxia-induced cell death. In contrast to prior work, our methods do not rely on cycling, regeneration, immigration or neovascularization. Rather, we have found a distinct effect, that proximately administered SDF-1α alters the metabolism of ischemic cells so that they can better withstand hypoxia. Our cardioprotective effect is observed within 24 hrs of the onset of hypoxia; hence, in our methods the SDF-1α must be administered prior to hypoxia induced cell death, and prior to the signaling events that lead to cycling, regeneration, etc.

BRIEF SUMMARY OF THE INVENTION

A prophylactic, cell-free method of preserving hypoxic tissue comprises the step of administering to the tissue an effective amount of stromal cell-derived factor-1 alpha (SDF-1α) before hypoxia induces cell death in the tissue.

In one embodiment the tissue is in a patient and the hypoxia is ischemic. In various further embodiments, the hypoxia results from an ischemic myocardial infarction, and the tissue is myocardium immediately surrounding the infarct zone; from an ischemic stroke; and from cardiac arrest. In a specific embodiment the tissue is in a patient, the hypoxia results from cardiac arrest, and the SDF-1α is administered prior to or during cardiopulmonary resuscitation (CPR) of the patient. In another embodiment, the tissue is transplant tissue in a patient, and the hypoxia results from transplantation-associated ischemia. In another embodiment, the tissue is in a patient, the hypoxia results from cardioplegia induced during coronary bypass surgery, and the SDF-1α is administered during the surgery.

In various embodiments the tissue is in a patient, and the SDF-1α is administered intravenously, or by injection into the tissue.

In one embodiment the tissue is isolated from a donor and prior to transplantation into a recipient the tissue is maintained in a tissue preservation solution containing the SDF-1α.

In various embodiments the SDF-1α is administered within 24 hours, 12 hours, 6 hours, 3 hours, or 1 hour of onset of the hypoxia.

In one embodiment the method further comprises the subsequent step of detecting a resultant preservation of the tissue, preferably within 36 hours or 24 hours of onset of the hypoxia.

In one embodiment the method of further comprises the prior step of detecting the hypoxia.

In one embodiment of the method a composition is administered that consists essentially of the amount of SDF-1α.

Another aspect of the invention is a composition comprising a tissue preservation solution and an effective amount of SDF-1α, and optionally a tissue isolated from a donor, and subject to hypoxia. In particular embodiments, the tissue preservation solution is selected from the group consisting of Euro Collins, Viaspan, Celsior, and Custodiol.

DETAILED DESCRIPTION OF THE INVENTION

The invention provides methods and compositions for using stromal cell derived-factor-1 alpha (SDF-1α) to preserve hypoxic tissue. The subject methods are prophylactic and cell-free and generally comprise or consist essentially of the step of administering to hypoxic tissue an effective amount of SDF-1α before hypoxia induces cell death in the tissue or other adverse outcomes. The subject compositions include SDF-1α medicaments formulated for delivery according to the disclosed methods, and SDF-1α-containing tissue preservation solution. SDF-1α, which is also known as CXCL12 (for chemokine (C-X-C motif) ligand 12), is a well-characterized chemokine. Purified or recombinant human SDF-1α is commercially available from several vendors (e.g. Biodesign International (Saco, Me.), BioSource International (Camarillo, Calif.), Calbiochem (EMD Biosciences, Merck KGaA, Darmstadt, Germany) and R&D Systems (Minneapolis, Minn.)).

Prior work on SDF-1α has focused on its chemotactic properties and its ability to recruit transplanted precursor cells to tissue damaged by hypoxia so that the transplanted cells regenerate the tissue (e.g. ref. 19 and Yamaguchi, 2003). Our method is "cell-free" in that it is not used in conjunction with cell therapy. We have discovered that SDF-1α has cytoprotective properties when administered to tissue concurrent with or soon after the onset of the hypoxia, and can prevent hypoxia-induced cell death and/or other adverse hypoxia-induced outcomes, overcoming the need for cell transplantation therapy. Hence, we use SDF-1α to directly alter the metabolism of ischemic cells so that they can better withstand hypoxia, providing entirely distinct targets and delivery protocols than previously described chemotaxis-based therapies.

The hypoxia may be ischemic or hypoxemic, and the tissue may be in situ in a patient or in vitro, such as in the case of a donor organ in storage or transit prior to implantation. In various embodiments, the tissue is in a patient and the hypoxia is ischemic. For example, the hypoxia may result from an ischemic myocardial infarction, and the tissue preserved by SDF-1α administration is the myocardium proximate to and immediately surrounding the infarct zone. As another example, the hypoxia may result from an ischemic stroke, and the tissue preserved by SDF-1α administration is brain tissue. In various other embodiments the hypoxia results from cardiac arrest, including intentional cardiac arrest (e.g. cardioplegia) induced during heart surgery, and the tissue is heart tissue or other tissue subject to hypoxia due to the lack of blood flow (e.g. splanchnic hypoxia). In another embodiment, the tissue is transplant tissue in a patient, and the hypoxia results from transplantation-associated ischemia, preferably wherein SDF-1 administration to the transplant during the transplantation surgery and/or within 36 hours and preferably within 24 hours of the surgery reduces incidents of transplant failure due to transplant ischemia.

In the administering step, the SDF-1α may be directly contacted with the tissue, and for tissue in situ, the SDF-1α can be administered to a patient by any route/means that allows the SDF-1α to reach the target tissue. In various embodiments, the SDF-1α is administered to a patient orally, by intravenous (i.v.) bolus, by i.v. infusion, intracranially, intraperitoneally, intraventricularly, intracardially, by epidural, etc. The SDF-1α can be prepared as a pharmaceutical composition admixed with conventional pharmaceutically-acceptable carriers. The composition may comprise other active agents for treating the hypoxia or the underlying cause of the hypoxia. For example, in the treatment of hypoxia resulting from myocardial infarction, the composition may additionally comprise tissue plasminogen activator or other blood clot dissolving medication. The composition may consist essentially of the amount of SDF-1α. For in vitro applications the tissue is typically maintained in a preservation solution containing the SDF-1α, such as described in more detail below and in Example 6. In the case of donor tissue transplantation, the tissue may be perfused with an SDF-1α-containing preservation solution, removed from the donor, and then maintained in a tissue preservation solution containing the SDF-1α until the tissue is transplanted into a recipient. Once transplanted into the recipient, the tissue may be further contacted with SDF-1α directly or indirectly (e.g. by i.v. administration to the transplant recipient).

It is generally desirable to administer the SDF-1α as soon as possible after the onset of hypoxia to prevent or minimize the occurrence of hypoxia-induced cell pathology, particularly irreversible cell pathology. Usually, the SDF-1α is administered within 48 hours of onset of the hypoxia, preferably within 36 hours, and more preferably within 24, 12, 6, or 3 hours. In most cases the SDF-1α is ideally administered within 1 hour of the onset of the hypoxia. In cases where it is known in advance that a tissue will be subject to hypoxia (e.g. during organ transplantation, cardioplegia, etc), the SDF-1α may be administered immediately prior to or concurrent with the conditions that result in the hypoxia. Because SDF-1α has a short half-life, in such cases it is preferable to administer the SDF-1α no sooner than 1 hour prior to the onset of the hypoxia, and preferably less than 30 minutes prior. In various embodiments, the administration of the SDF-1α may be coordinated with other treatments for the hypoxia or the underlying cause of the hypoxia. For example, in the case of cardiac arrest, the SDF-1α may be administered to the patient prior to or during cardiopulmonary resuscitation (CPR) of the patient. In the case of hypoxia resulting from cardioplegia induced during coronary bypass surgery, the SDF-1α may be administered during the surgery, e.g. cardioplegia medium or cocktail is supplemented with SDF-1α, and infused directly into the coronary arteries.

An effective amount of SDF-1α provides a demonstrable cytoprotective effect and significantly reduces, and preferably prevents hypoxia-induced pathology. Examples of such pathology include the cell death that occurs after myocardial or cerebral infarction, atrial fibrillation that occurs after coronary artery bypass graft surgery, reduced organ function that occurs after organ transplantation, etc. The method of the invention may further comprise the subsequent step of detecting a resultant preservation of the tissue, for example as evidenced by decreased cell death in the tissue, improved organ function, etc. Various known methods that can be used to demonstrate the preservative effect of SDF-1α on hypoxic tissue such as echocardiography, measurement of infarct size, etc. In one embodiment, the detecting is performed between 24 and 48 hours of onset of the hypoxia.

An effective amount of SDF-1α, when administered directly to the tissue is typically in the range of about 30 to 3,000 ng, preferably 100 to 1000 ng, such as about 200, 300 or 500 ng; when systemically administered, an effective amount is typically in the range of about 15 to 1,500 ug, preferably about 50 to 500 ug, such as 100, 150 or 200 ug. The SDF-1α is often administered as a single bolus dose, although in cases of prolonged hypoxia it may be preferred to administer the SDF-1α by continuous infusion or in several doses spaced through the duration of the hypoxia. As the primary protective benefit of SDF-1α treatment is seen early on, treatment with SDF-1α often ceases within 48 hours of the onset of the hypoxia, and usually within 24 or 12 hours of the onset of the hypoxia. Dosages and treatment protocols for various causes of hypoxia are optimized through routine clinical practice.

The subject methods may further comprise the prior step of detecting the hypoxia. For example, hypoxemic hypoxia can be detected using known methods for measuring tissue partial oxygen tension ($PO_2$) such as dynamic fluorescence quenching (Shaw, 2002), polarographic electrode technique (Shaw, 2002), electron paramagnetic resonance (EPR) oximetry (Swartz, 2004; Swartz et al. U.S. Pat. No. 5,494,030), etc. Ischemic hypoxia can be detected by measuring lactate/pyruvate ratios (Contaldo, 2005) or microvascular blood flow (De Backer, 2002). Levels of glutamate and lactate are early markers of cerebral ischemia (Sarrafzadeh, 2000). Troponin and creatine kinase-MB are markers of myocardial infarction. Alternatively, hypoxia can be detected inferentially through the observation of symptoms associated with hypoxia in the tissue or prior knowledge that the tissue has been subjected to a hypoxia-inducing event.

Another aspect of the invention is a composition comprising a tissue preservation solution and an effective amount of SDF-1α. Tissue preservation solutions are well-known in the art for perfusion and/or storage of tissue and typically comprise electrolytes, a buffer, an osmotic agent and optionally energy substrates and anti-oxidants (see e.g. Mateo, 2002, for the compositions of several widely-used preservation solutions). Examples of commercially available tissue preservation solutions include Custodiol® HTK Solution, Viaspan® (UW Solution), Euro-Collins® solution, ET-Kyoto solution, Celsior® solution, and Hypothermosol®. Effective amounts of SDF-1α prolong the duration that a tissue subject to hypoxia can be maintained in the preservation solution before hypoxia-induced cell death occurs and/or improve the survival rate and/or function of donor organs maintained in the solution prior to transplantation. In preferred embodiments, a tissue subject to hypoxia can be maintained in the SDF-1α-containing solution without hypoxia-induced cell death for at least 10%, preferably at least 25%, and more preferably at least 50% longer than a tissue maintained in the same solution without SDF-1α. Suitable concentration ranges are typically about 1 to 100 ug/ml, preferably about 2 to 50 mg/ml, such as 5, 10 or 25 mg/ml. The SDF-1α-containing solution is used in the same manner as conventional tissue preservation solutions such as for flushing (e.g. perfusion) the tissue at the time of removal from a donor in preparation for storage, and during storage and transportation. The composition of the invention may further comprise a tissue isolated from a donor, and subject to hypoxia. In certain embodiments, the tissue is a solid organ selected from heart, kidney, liver, lung, pancreas, and small bowel.

Example 1

SDF-1α Preserves Cardiac Function After Infarction by Promoting Survival of Ischemic Myocardium To test the hypothesis that SDF-1α protein could improve cardiac function post-infarction, we created ligations of the left anterior descending coronary artery in adult male mice to prevent blood flow to a portion of the left ventricle, creating a zone of injury. Injections of PBS or SDF-1α were administered into myocardium at two sites near the infarct zone. Mice were then subjected to echocardiography at various timepoints to measure cardiac function by assessment of fractional shortening (FS) and ejection fraction (EF). All studies and analyses of data were performed in blinded fashion.

We created myocardial infarctions in adult male mice by ligation of the left anterior descending coronary artery (30), and treated half with SDF-1α and half with PBS. At 14 days post-infarction, left ventricles of PBS-treated mice had a mean FS of 27.9+/−1.5% (n=9), while SDF-1α treatment resulted in a mean FS of 38.1+/−1.5% (n=11; P<0.0001). As a second measure of venitricular function, two-dimensional echocardiographic measurements revealed that the mean fraction of blood ejected from the left ventricle (EF) in PBS-treated mice was 35.0+/−7.9% (n=7), compared to a mean of 61.9+/−3.7% (n=8; P<0.0001) in SDF-1α-treated mice. At 28 days after infarction, when additional ventricular remodeling has occurred and the scar is typically well formed, we observed a similar trend in cardiac function of SDF-1α-treated mice. FS was 26.8+/−1.2% (n=9) for the PBS group and 39.2+/−2.9% (n=11; P<0.0001) for the SDF-1α group, while EF was 31.5+/−3.5% (n=7) and 48.8+/−2.4% (n=8; P<0.0001) for PBS and SDF-1α groups, respectively. Cardiac function remained depressed relative to sham-operated animals (~60% FS; ~75% EF). The improvement at 28 days in FS or EF (46% and 55%, respectively) upon SDF-1α treatment corresponded to echocardiographic findings that the end diastolic dimensions (EDD) and end systolic dimensions (ESD) were both significantly smaller in the SDF-1α group, indicating that SDF-1α treatment had resulted in increased cardiac function and decreased cardiac dilation after infarction. Histological analysis revealed a marked reduction in the size of the scar tissue area and therefore a thicker functional anterior wall of the heart. Approximately 6 weeks after infarction, the percent scar tissue was 10.4+/−2.7% in PBS treated controls and 2.4+/−1.2% in SDF-1α-treated animals (P<0.001). As the scar tissue became more organized by 9 weeks post-infarction, scar tissue domains in PBS- or SDF-1α-treated hearts represented 22.2+/−5.6% and 4.6+/−2.8% of total area, respectively (P<0.001).

The functional and histologic improvements observed with the single administration of SDF-1α immediately after coronary ligation indicated that the beneficial effects of SDF-1α occur in the early stages following infarction. We therefore sought to determine the timeframe of functional improvement by performing echocardiography at numerous time points within days of the coronary ligation. At 1 day after infarction, we found that FS was 32.2+/−1.6% (n=8) with PBS treatment compared to 40.2+/−1.6% (n=8, P<0.0001) with SDF-1α treatment; correspondingly, EF was 40.7+/−2.7% (n=8) or 56.6+/−3.7% (n=8, P<0.0001), respectively. This pattern continued 3 days post-infarction as SDF-1α treated mice again demonstrated significant improvement in FS and EF.

SDF-1α-mediated functional improvement occurred as early as 24 hours post-infarction and continued 3, 14, and 28 days post-infarction. We performed parallel experiments with thymosin β4 to investigate the comparative efficacy of SDF-1α and found that improvement of cardiac function after coronary ligation was similar with SDF-1α or thymosin β4. The combination of SDF-1α and thymosin β4 appeared to have no greater effect than either one alone.

Our previous data with thymosin β4 indicate that it functions in a cardioprotective fashion within 24 hours after infarction rather than through recruitment or promotion of stem cells. However, there are reports suggesting that SDF-1α can attract CXCR4-expressing hematopoietic stem cells to the heart, where they are assumed to take up residence and improve cardiac function (19, 20). The mechanism by which the stem cells might improve function remains unclear. Recent studies have suggested that secreted signals arising from stem cells may potentiate cardiac regeneration or repair or even rescue congenital heart defects (21, 22).

To determine whether SDF-1α recruitment of stem cells into the heart might play a role in its beneficial effects after infarction, we examined levels of c-kit-positive hematopoietic stem cells in the heart after coronary ligation. We did not observe any difference in the number of c-kit-positive cells in control versus SDF-1α-treated hearts at 72 hours post-infarction; even fewer c-kit-positive cells were seen 24 hours post-infarction and again the numbers were comparable with or without SDF-1α. In addition, there was no evidence of proliferating cells in the area of damaged myocardium. The lack of evidence for increased stem or proliferating cells upon. SDF-1α exposure is consistent with the rapid improvement in cardiac function within 24 hours, which is too early for stem cell differentiation into mature, large myocytes.

To further investigate the mechanism by which SDF-1α induces cardiac repair, we examined the degree of cell death in the direct area of infarction and the neighboring area of hypoxic myocardium. Apoptotic cells marked by TUNEL assay were observed in both control and SDF-1α-treated hearts during the first 24 hours, and were largely isolated to the immediate area of infarct. However, by 72 hours post-infarction, the apoptosis had spread outside of the immediate area of infarction to surrounding myocardial tissue in all directions in the control PBS-treated hearts. In contrast, the SDF-1α-treated hearts showed little or no apoptosis outside of the area of infarct. Costaining with muscle actin confirmed that cells undergoing apoptosis were indeed myocytes. Thus, bordering myocardium that is normally irreparably damaged post-infarction is protected by SDF-1α-directed cell survival.

While the cardioprotective effects of SDF-1α may aid in survival of hypoxic myocardium, the myocytes ultimately would need to be vascularized to achieve long-term survival. Hence, we investigated the degree of neo-angiogenesis in the presence of SDF-1α. An antibody to isolectin B4, a known marker of endothelial cells in the microvasculature, demonstrated a significant increase in the number of capillaries in the area of injury in SDF-1α-treated hearts compared to PBS-treated hearts within 72 hours. Quantitation of the isolectin B4-positive capillaries revealed an approximately 93% increase in microvasculature over controls. This observation was validated with two other endothelial markers, PECAM and vWF.

Our previous observations of ILK and Akt activation upon thymosin β4 treatment and SDF-1α's known effects on Akt led us to investigate the response of this pathway in infarcted hearts exposed to SDF-1α. Like thymosin β4, in harvested heart cell lysates, SDF-1α showed increased levels of ILK protein and phosphorylation of its downstream kinase Akt/PKB upon SDF-1α treatment. These changes were observed within 24 hours after coronary ligation and more prominently at 72 hours. Vascular endothelial growth factor (VEGF), a known regulator of angiogenesis, was similarly upregulated in response to SDF-1α, consistent with the increase in capillary density described above.

Our data show that SDF-1α, a secreted chemokine that activates Akt, has cell protective properties under conditions of cardiac tissue hypoxia. After acute myocardial infarction, SDF-1α treatment resulted in decreased cell death, and increased angiogenesis within the hypoxic tissue, ultimately leading to reduced scarring and improved cardiac function. Phosphorylation of Akt was increased in vivo as was upregulation of VEGF in response to SDF-1α, providing potential mechanisms for the observed effects of SDF-1α.

Published reports have alluded to the potential role of SDF-1α in cardiac regeneration and have focused on attraction of bone marrow-derived somatic stem cells to the heart postinfarction (19, 20). Recent studies, however, have raised considerable doubt regarding the potential of bone marrow-derived stem cells to transdifferentiate into cardiomyocytes (23-25), although they may provide a non-cell autonomous benefit via secreted factors. Whether or not SDF-1α induces regeneration and thereby improves cardiac function after an acute insult had not been previously addressed, but the notion of recruitment of stem cells into an infarcted tissue has been suspected. While we do not rule out a role for SDF-1α in controlling stem cell-based improvement in cardiac function over time, our studies show that the improvement of heart function at both 24 and 72 hours post-infarction is too soon to be accounted for by stem cell differentiation. Multiple published accounts of putative stem cell differentiation in the heart report times ranging from 9 to 20 days post-infarction at the earliest (26-28). Consistent with this, we did not find evidence for increased number of stem cells or proliferating cells upon SDF-1α treatment.

Our data indicate that the initial conservation of function upon SDF-1α treatment is due to preservation of myocardial tissue bordering the immediate area of infarct. This preservation may occur through an Akt-mediated pathway or other SDF-1α dependent mechanisms and appears unrelated to stem cell recruitment and differentiation. A recent report demonstrated that Akt1 is essential for proper angiogenesis both post-ischemia and post-VEGF activation (29).

Example 2

Administration of SDF-1α to Reduce Infarct Size in Patients Undergoing Primary Percutaneous Coronary Angioplasty for ST-Segment Elevation Myocardial Infarction Methodology for this clinical study is adapted from ClinicalTrials.gov identifier NCT00149058 entitled "A Phase II Randomized Trial to Investigate the Safety and Efficacy of Recombinant Human Erythropoietin on Infarct Size in Patients Undergoing Primary Percutaneous Coronary Angioplasty for ST-Segment Elevation Myocardial Infarction". This randomized double-blind, placebo-controlled clinical trial examines the effects of recombinant human SDF-1α given at the time of primary angioplasty for acute myocardial infarction (MI). The primary outcome is myocardial infarct size. Secondary outcomes are death and reinfarction.

The study comprises 124 subjects with acute ST-elevation MI who fulfill the inclusion/exclusion criteria and give informed consent to participate in the study. Subjects are given a single intravenous bolus of SDF-1α 350 mg or placebo and then undergo primary percutaneous coronary angioplasty (primary PCI) according to standard clinical protocols. Placebo is identical to SDF-1α without the active ingredient. After the PCI subjects receive standard care on the coronary care unit. Subjects receive gadolinium enhanced cardiovascular magnetic resonance (CMR) performed before discharge to evaluate infarct size. Follow-up is performed at 30 days (clinical, ECG and 20 ml blood sample) and at 90 days (clinical, ECG and CMR scan and blood sample). The study ends at 90 days and patients continue with standard clinical care under the direction of a consultant cardiologist.

CMR is performed using a 1.5 tesla scanner according to standard protocols. Each scan lasts about 1 h and information is collected on tissue characteristics, left ventricular function, wall motion abnormalities, and myocardial perfusion. Myocardial infarcts are detected by late contrast gadolinium enhancement. Gadolinium is used at doses up to 0.2 mmol/kg and is safe with an incidence of mild and transient side effects including headache and nausea of ~1%. Scans are performed under continuous ECG monitoring with a doctor and at least 1 other person present. Resuscitation facilities are available at all times and the MRI facility is covered by an experienced 24 hour a day cardiac arrest team.

Inclusion Criteria: Male or female >18 years of age; Weight between 50 kg and 120 kg; Suspected of having his/her first-documented STEMI; Symptoms of ischemia of >20 min with <6 h prior to PCI; Either 1 mm ST elevation in at least two contiguous limb leads or >2 mm ST elevation in 2 contiguous chest leads; Primary PCI to occur within 8 h from the onset of symptoms; and Women of childbearing potential must have a negative pregnancy test.

Exclusion Criteria: Contraindications to MRI scanning; history or ECG evidence of previous STEMI; cardiogenic shock; NYHA class III-IV heart failure; LBBB or AF on ECG; major trauma; major surgery, eye, spinal cord, or brain surgery within the last 3 months; significant hepatic disturbance; chronic renal impairment (Creatinine >200 µmol/L); stroke or TIA <6 months; pregnancy or breast-feeding; dependence on alcohol or other DOA; significant psychiatric/neurologic disease that would prevent adherence to the requirements of the protocol; significant immunocompromise (including, but not limited to AIDS and immune-suppressive therapy; current hemodialysis or peritoneal dialysis.

Results: A significant reduction in myocardial infarct size in SDF-1α-treated versus placebo-treated patients demonstrates the cardio-protective effect of SDF-1α treatment for ischemic myocardial infarction.

Example 3

Perioperative Administration of SDF-1α for the Prevention of Postoperative Atrial Fibrillation in Patients Undergoing Coronary Artery Bypass Surgery Atrial fibrillation (AF) is the most common complication following coronary artery bypass graft (CABG) surgery. AF is sign of tissue hypoxia and often occurs in conjunction with depressed cardiac function post-operatively. This study, adapted from the GAP study: "Giving IV and Oral Amiodarone Perioperatively for the Prevention of Postoperative Atrial Fibrillation in Patients Undergoing Coronary Artery Bypass Surgery" (Kerstein, 2004), demonstrates the ability of perioperative SDF-1α treatment to prevent postoperative atrial fibrillation in CABG patients.

Patient Population: 50 patients scheduled for coronary artery bypass graft surgery (CABG) are randomly selected for participation in the SDF-1α trial. Parameters monitored include ejection fraction (EF), age, gender, weight, height, left atrial size, bypass time, cross-clamp time, on cardiopulmonary bypass (CPB) or off CPB, length of stay, and treatment with β-blockers, digoxin, and calcium-channel blockers. Cardiac risk factors including hypertension, diabetes, smoking, family history of coronary artery disease, history of previous myocardial infarction, congestive heart failure, COPD, or cerebrovascular accident in the past are also compared.

To qualify for participation in the study, the patient is at least 18 years old, able to give informed consent, is scheduled for CABG only, has had normal sinus rhythm at the time of enrollment, and has no history of atrial fibrillation. Exclusion criteria include use of antiarrhythmic agents other than β-blockers, calcium-channel blockers, or digitalis, patients with thyroid disease, abnormal liver function test results, pregnancy, resting sinus bradycardia in the absence of medical therapy, or uncontrolled heart failure.

Study Protocol: All patients in the study are evaluated for left ventricular (LV) function (using echocardiography, multiple gated acquisition scan, or coronary angiography). Baseline thyroid function tests and liver function tests are performed on all patients, and cardiac function and pulmonary function tests including diffusion and lung capacity are performed as clinically warranted. SDF-1α-supplemented (10 ug/ml) cold blood cardioplegia is used during the surgery. After surgery the patients are transferred to the cardiothoracic ICU and subsequently to a telemetry step-down unit. Patients are continuously monitored with ECG telemetry equipment until the time of discharge. Patients are evaluated on a daily basis until discharge by one of the investigators, and the telemetry record is reviewed daily. An episode of atrial fibrillation is considered to have occurred if the arrhythmia persists for at least 30 min, or <30 min if it leads to hemodynamic instability requiring intervention. Management of the arrhythmia is left to the discretion of the cardiac surgery team. All patients are followed up from the time of surgery to the time of discharge. β-blockers are continued during the perioperative period in all patients unless a contraindication developed or the private physician discontinues it. The option to perform surgery on or off CPB is left to the discretion of the surgeon.

Study End Point: The primary study end point is onset of atrial fibrillation lasting >30 min or earlier warranting symptomatic treatment; secondary end points are surgery on or off CBP, length of hospital stay, and cost of hospitalization.

Example 4

Neuroprotective Effect of SDF-1α in Animal Models of Focal Brain Ischemia and Concussive Brain Injury This study uses previously described methods (Brines et al, 2000) to demonstrate the neuroprotective effect of systemically administered SDF-1α in animal models of focal brain ischemia and concussive brain injury resulting in increased intracranial pressure and decreased arterial perfusion.

Middle Cerebral Artery (MCA) Occlusion. Sprague-Dawley male rats weighing ~250 g are anesthetized with pentobarbital [60 mg/kg body weight (BW)]. Body core temperature is thermostatically maintained at 37° C. by using a water blanket and a rectal thermistor (Harvard Apparatus) for the duration of the anesthesia. The carotid arteries are visualized, and the right carotid is occluded by two sutures and cut. A burr hole adjacent and rostral to the right orbit allows visualization of the MCA, which is cauterized distal to the rhinal artery. Animals are then positioned on a stereotaxic frame. To produce a penumbra surrounding this fixed MCA lesion, the contralateral carotid artery is occluded for 1 h by using traction provided by a fine forceps. SDF-1α(30 ul of a 0.1 □g/ul solution) or saline control is administered at 0 hr, 3 hr, 6 hr, or 12 hr from the onset of the reversible carotid occlusion. To evaluate the extent of injury, the animals are killed after 24 h, the brains are removed, and serial 1-mm thick sections through the entire brain are cut by using a brain matrix device (Harvard Apparatus). Each section is then incubated in a solution of 2% triphenyltetrazolium chloride (wt/vol) in 154 mM NaCl for 30 min at 37° C. and stored in 4% paraformaldehyde until analysis. Quantification of the extent of injury is determined by using a computerized image analysis system (MCID, Imaging Research, St. Catharine's, ON, Canada). To accomplish this, a digital image of each section is obtained and the area of injury delineated by outlining the region in which the tetrazolium salt is not reduced, i.e., nonviable tissue. For cases in which the necrosis is so severe that tissue is actually lost and therefore the borders can not be directly assessed, an outline of the contralateral side is used to estimate the volume of injured brain. Total volume of infarct is calculated by reconstruction of the serial 1-mm thick sections. A reduction in the volume of brain infarcted 24 h after ischemia in SDF-1α treated versus control demonstrates the protective effect SDF-1α has on brain tissue subject to focal ischemic stroke.

Blunt Trauma. A mechanical insult delivered to the brain elicits elements of ischemic, excitotoxic, and inflammatory injury and, if severe enough, produces a cavitary lesion after 7-10 days (Brines, 2000). To produce severe trauma to the temporal and frontal cortices reproducibly, a pneumatic piston is precisely driven by using miniature precision valves (Clippard, Cincinnati, Ohio) powered by nitrogen. Displacement and velocity of the piston is determined by a digital motion detector (EPD Technologies, Elmsford, N.Y.). Female BALB/c mice are anesthetized with pentobarbital, and their heads are placed securely in a stereotaxic frame. A scalp incision is made to locate the bregma. A 3-mm diameter stainless steel piston is then positioned to deliver the blow 2 mm caudal and 2 mm ventral to the bregma. Once the piston is activated, the velocity and time of impact is noted, as well as the amount of damage to the skull. The scalp incision is closed by using sutures. SDF-1α is administered at the time of, or 3, 6, or 12 h after impact. Ten days after impact, the animals are anesthetized with pentobarbital and their brains are fixed by perfusion of 4% paraformaldehyde. The brains are then embedded in paraffin and 20-mm sections are cut through the region of injury and stained with hematoxylinyeosin. Quantitative analysis of volume of injury is determined by using the MCID system as described above. Qualitative analysis of degree of inflammatory infiltrate is performed by a blinded observer scoring each slide by using a scale of 0-5, 0 corresponding to no visible inflammation and 5 to the densest infiltrate. Extensive cavitary injury 10 days after infliction of blunt trauma is seen in control animals. A reduction in the extent of injury in SDF-1α treated animals demonstrates the protective effect SDF-1α has on brain tissue subject to traumatic injury.

Example 5

Effect of SDF-1α on Ischemia-Reperfusion Injury in Transplanted Hearts

This study utilizes a previously described ex vivo perfusion system (Smolenski, 2001) to evaluate the protective effect SDF-1α has on transplanted hearts and its ability to ameliorate symptoms of ischemia-reperfusion injury.

All animals receive humane care in compliance with the Guide for the Care and Use of Laboratory Animals published by the National Institutes of Health (NIH publication No. 85-23, revised 1985). Male Sprague-Dawley rats (275 to 300 g) are used as both the donors and the recipients. Donor rats are anesthetized with diethyl ether and heparinized (200 IU/kg IV). The abdominal and chest cavities are opened, and hearts are collected after the in situ infusion of 30 mL St Thomas' Hospital No. 1 cardioplegic solution (supplemented with 10 ug/ml SDF-1α in treatment groups I and II) through the abdominal aorta. The cardiac veins are ligated and the hearts are collected and stored in cardioplegic fluid for 4 hours at 4° C. Then, hearts are heterotopically transplanted into the abdomen of recipient rats. The recipient rat is anesthetized with pentobarbital (50 mg/kg IP), the abdominal cavity is opened, and the aorta of the donor heart is anastomosed to the side of the recipient's abdominal aorta. The pulmonary artery of the donor heart is anastomosed to the side of the inferior vena cava. The transplantation procedure is completed within 20 minutes. In treatment groups II and III, SDF-1α is administered (5 ug/g rat in 30 ul total volume solution) into the peritoneal cavity at the time the abdomen is closed. In the control groups, 0.9% saline is administered at the same volume.

After transplantation, hearts are collected either after 1 hour or the rats are allowed to recover and are maintained for 24 hours. Rats are anesthetized with diethyl ether and heparinized (200 IU) via the femoral vein. The abdominal cavity is opened, and the hearts are rapidly excised, placed in ice-cold perfusion buffer, and immediately attached to a Langendorff perfusion system. The hearts are then perfused with filtered (0.45-μm pore size) Krebs-Henseleit buffer solution at a constant pressure of 85 mm Hg at 37° C. The buffer solution contains (in mmol/L) NaCl 118, KCl 4.7, $MgSO_4$ 1.2, $KH_2PO_4$ 1.2, $NaHCO_3$ 24, glucose 11, and $CaCl_2$ 1.4 and is continuously gassed with 95% $O_2$/5% $CO_2$ Assessment of mechanical function is made using a balloon catheter inserted into the left ventricle and connected to a pressure transducer linked to a PC-based data acquisition and processing system (AcqKnowledge; Biopac Systems Inc). The balloon is inflated with incremental volumes of water from 0 to 250 μL (50 μL each step). Pressure recordings are used to construct left ventricular systolic pressure (LVSP) and left ventricular end-diastolic pressure (LVEDP) volume relations. A difference between LVSP and LVEDP is used to calculate left ventricular developed pressure (LVDP). The maximum value of LVDP is used for further calculations. Other information, such as heart rate, maximum value of +dP/dt, and minimum value of −dP/dt, are derived from recorded data. Coronary flow is continuously recorded with an electromagnetic flowmeter (Nihon-Kohden).

Activity of the neutrophil marker enzyme myeloperoxidase is measured in homogenates of hearts freeze clamped after functional assessment at the end of Langendorff perfusion. Concentrations of nucleotides and creatine metabolites are measured in hearts using reversed-phase HPLC as described in detail previously (Smolensky, 1990) except that freeze-clamped hearts are freeze dried and extracted with 0.4 mol/L perchloric acid. After neutralization, samples are analyzed with the Agilent 1100 HPLC system.

Statistical analysis of the differences in systolic and diastolic pressure-volume relations is made with 2-way ANOVA, followed by the Student-Newman-Keuls test. Changes in myeloperoxidase activity, metabolite concentration, developed pressure, +dP/dt, and −dP/dt are analyzed using 1-way ANOVA, followed by the Student-Newman-Keuls test. Differences were considered significant at $P<0.05$.

Improvements in both systolic and diastolic functions in SDF-1α-treated transplanted hearts versus control hearts after 24 hours of reperfusion demonstrates the protective effect of SDF-1α treatment in both the donor and recipient animals. Attenuation of neutrophil infiltration as indicated by reduced activity of myeloperoxidase in treated hearts is indicative of a reduction in postischemic inflammation.

Example 6

Clinical Study Comparing Tissue Preservation Solution with and without SDF-1α

This clinical study, adapted from an ongoing trial described by Nardo et al, 2005, compares Celsior® solution (CEL) with and without added SDF-1α in liver preservation for transplantation.

To have comparable groups of patients, the following entry criteria for the study are used: (1) recipient aged up to 65 years; and (2) first elective whole or split liver transplantation. Exclusion criteria are: (1) retransplant; (2) emergency liver transplant; (3) domino and living liver transplantation; and (4) whole liver combined with any other organ. In a single transplant center, 40 livers are randomized to CEL (n=20) or CEL+SDF-1α (n=20) preservation solution. The compositions of CEL and CEL+SDF-1α are shown in Table I.

TABLE I

| Content (mmol/L) | CEL | CEL + SDF-1α |
|---|---|---|
| Lactobionate | 80 | 80 |
| Mannitol | 60 | 60 |
| Glutamate | 20 | 20 |
| Histidine-Buffer | 30 | 30 |
| Glutathion | 3 | 3 |
| Allopurinol | 1 | 1 |
| $Na^+$ | 100 | 100 |
| $K^+$ | 15 | 15 |
| $Mg^{++}$ | 13 | 13 |
| $Ca^{++}$ | 0.25 | 0.25 |
| SDF-1α | 0 | 10 ug/ml |
| Ph | 7.3 | 7.3 |
| Osmolality (mOsM) | 360 | 360 |

The solution is chosen in a random fashion after a liver has been offered and accepted and the recipient is considered transplantable. Following randomization, livers are perfused in situ via aorta and portal vein with CEL or CEL+SDF-1α solution. Total perfusion volumes are 30 mL/kg via portal vein and 60 mL/kg via aorta. After the harvest procedure, livers are stored at 4° C. until transplantation. Donor liver biopsy is performed when the ultrasonography scan shows steatosis or on the basis of the clinical evaluation by the harvest surgeon.

The main donor and graft variables and the recipient demographic and clinical characteristics are evaluated in the two study groups. The following parameters are tracked: donor: age, gender, cause of death, intensive care unit stay in days, dopamine yamma (mg/kg/min), and no. of donors with hypotension episodes; graft: steatosis (mild/moderate/severe), cold ischemia time (min), warm ischemia time (min); and recipient: age, gender, UNOS Status (1/2A/2B/3).

The following intra- and postoperative course parameters in recipient liver transplantation are tracked: autologous red blood cells i.o. (mL); homologous red blood cells i.o. (mL); fresh frozen plasma i.o. (mL); intensive care unit stay (days); AST (U/L) at days 1, 3 and 7; ALT (U/L) at days 1, 3 and 7; T. bilirubin (mg/mL) at days 1, 3 and 7; PT (%) at days 1, 3 and 7; primary nonfunction; initial poor function; hepatic artery thrombosis; biliary stenosis; rejections with first month; retransplantations, and graft/patient survival at 1, 3, and 12 months.

Acute rejection is diagnosed by clinical signs such as fever and an increase of transaminases and bilirubin, with or without morphological signs of rejection in biopsy. Liver biopsies are performed in the postoperative course if clinically indicated. Statistical analysis is performed using Student's t test and chi-square test to assess differences between study values. P values less than 0.05 are regarded as statistically significant.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

REFERENCES

1. Braunwald, E. 1997. *N Engl J Med* 337:1360-1369.
2. Jessup, M., and Brozena, S. 2003. *N Engl J Med* 348:2007-2018.
3. Bhatia, G., et al. 2005. *Expert Rev Cardiovasc Ther* 3:111-122.
4. Depre, C., and Vatner, S. F. 2005. *Trends Cardiovasc Med* 15: 101-110.
5. Mangi, A. A. et al. 2003. *Nat Med* 9:1195-1201.
6. Bock-Marquette, I., et al. 2004. *Nature* 432:466-472.
7. Bleul, C. C., et al. 1996. *J Exp Med* 184:1101-1109.
8. Aiuti, A., et al. 1997. *J Exp Med* 185:111-120.
9. Corcione, A., et al. 2000. *J Natl Cancer Inst* 92:628-635.
10. Doitsidou, et al. 2002. *Cell* 111:647-659.
11. Bajetto, A., et al. 2001. *J Neurochem* 77:1226-1236.
12. Kortesidis, A., et al. 2005. *Blood* 105:3793-3801.
13. Mirshahi, F., et al. 2000. *Thromb Res* 99:587-594.
14. Orimo, A., et al. 2005. *Cell* 121:335-348.
15. Porcile, C., et al. 2005. *Exp Cell Res* 308:241-253.
16. Vlahakis, S. R., et al. 2002. *J Immunol* 169:5546-5554.
17. Zou, W., et al. 2001. *Nat Med* 7:1339-1346.
18. Pillarisetti, K., and Gupta, S. K. 2001. *Inflammation* 25:293-300.
19. Abbott, J. D., et al. 2004. *Circulation* 110:3300-3305.
20. Askari, A. T., et al. 2003. *Lancet* 362:697-703.
21. Fraidenraich, D., et al. 2004. *Science* 306:247-252.
22. Yoshioka, T., et al. 2005. *Stem Cells* 23:355-364.
23. Balsam, L. B., et al 2004. *Nature* 428:668-673.
24. Murry, C. E., et al. 2004. *Nature* 428:664-668.
25. Nygren, J. M., et al. 2004. Nat Med 10:494-501.
26. Beltrami, A. P., et al. 2003. Cell 114:763-776.
27. Jackson, K. A., et al. 2001. J Clin Invest 107:1395-1402.
28. Orlic, D., et al. 2001. Nature 410:701-705.
29. Ackah, E., et al. 2005. J Clin Invest 115:2119-2127.
30. Garner, L. B., et al. 2003. Am J Physiol Heart Circ Physiol 285:H2500-2509.

Brines, M L et al, 2000, Proc Natl Acad Sci USA. 97:10526-31
Contaldo, C. et al, 2005, Anesth Analg 100:817-822
Damas, J K et al, 2002, Circulation. 106:36-42.
De Backer, D. et al, 2002, Am J Respir Crit Care Med. 166:98-104.
Kerstein, J. et al, 2000, Chest. 126:716-24.
Mateo, R. et al, 2002, Opin Organ Transplant 7:53-59
Nardo, B. et al, 2005, Transplant Proc. 37:320-2
Pitt, B. et al, 2003, N. Engl J. Med. 348:1309-1321
Sarrafzadeh, A S. et al, 2000, Neurosurg Focus 9; Article 2: p 1-6
Shaw, A D. et al, 2002, Crit Care. 6: 76-80.

Smolenski, R T et al, 1990 *J Chromatogr.* 527:414-420.
Smolenski, R T et al, 2001, Circulation. 104(12 Suppl 1):I246-52.
Swartz, H M. et al, 2004, NMR Biomed. 17:335-51
Yamaguchi, J. et al, 2003, Circulation. 107:1322-1328.

The invention claimed is:

1. A prophylactic, cell-free method of preserving hypoxic myocardium tissue in a patient and following ischemia, comprising the step of administering to the tissue an effective amount of stromal cell-derived factor-1 alpha (SDF-1α) before hypoxia induces cell death in the tissue.

2. The method of claim 1 wherein the tissue is in a patient and the hypoxia is ischemic.

3. The method of claim 1 wherein the tissue is in a patient, the hypoxia results from an ischemic myocardial infarction, and the tissue is myocardium immediately surrounding the infarct zone.

4. The method of claim 1 wherein the SDF-1α is administered intravenously.

5. The method of claim 1 wherein the SDF-1α is administered by injection into the tissue.

6. The method of claim 1 wherein the SDF-1α is administered within 24 hours of onset of the hypoxia.

7. The method of claim 1 wherein the SDF-1α is administered within 12 hours of onset of the hypoxia.

8. The method of claim 1 wherein the SDF-1α is administered within 6 hours of onset of the hypoxia.

9. The method of claim 1 wherein the SDF-1α is administered within 3 hours of onset of the hypoxia.

10. The method of claim 1 wherein the SDF-1α is administered within 1 hour of onset of the hypoxia.

11. The method of claim 1 further comprising the subsequent step of detecting a resultant preservation of the tissue.

12. The method of claim 1 further comprising the subsequent step of detecting a resultant preservation of the tissue within 48 hours of onset of the hypoxia.

13. The method of claim 1 further comprising prior to the administering step the step of detecting the hypoxia.

14. The method of claim 1 wherein administered is a composition consisting essentially of the amount of SDF-1α.

15. The method of claim 1 wherein the SDF-1α is administered directly to the tissue in the range of 30 to 3,000 ng.

16. The method of claim 1 wherein the SDF-1α is administered directly to the tissue in the range of 100 to 1000 ng.

17. The method of claim 1 wherein the amount of SDF-1α is administered systemically in the range of 15 to 1,500 ug.

18. The method of claim 1 wherein the amount of SDF-1α is administered systemically in the range of 50 to 500 ug.

19. The method of claim 1, wherein treatment with SDF-1α ceases within 48 hours of the onset of the hypoxia.

20. The method of claim 1, wherein treatment with SDF-1α ceases within 24 hours of the onset of the hypoxia.

21. The method of claim 1, wherein treatment with SDF-1α ceases within 12 hours of the onset of the hypoxia.

* * * * *